(12) United States Patent
Wiltberger et al.

(10) Patent No.: US 11,406,263 B2
(45) Date of Patent: *Aug. 9, 2022

(54) PHOTOMEDICAL TREATMENT SYSTEM AND METHOD WITH A VIRTUAL AIMING DEVICE

(71) Applicant: IRIDEX Corporation, Mountain View, CA (US)

(72) Inventors: Michael W. Wiltberger, Santa Clara, CA (US); Dan E. Andersen, Menlo Park, CA (US); David H. Mordaunt, Los Gatos, CA (US)

(73) Assignee: IRIDEX Corporation, Mountain View, CA (US)

( * ) Notice: Subject to any disclaimer, the term of this patent is extended or adjusted under 35 U.S.C. 154(b) by 29 days.

This patent is subject to a terminal disclaimer.

(21) Appl. No.: 16/705,947

(22) Filed: Dec. 6, 2019

(65) Prior Publication Data
US 2020/0107724 A1   Apr. 9, 2020

Related U.S. Application Data

(63) Continuation of application No. 11/588,451, filed on Oct. 27, 2006, now Pat. No. 10,524,656.
(Continued)

(51) Int. Cl.
| A61F 9/008 | (2006.01) |
| A61B 3/14 | (2006.01) |
| A61B 3/15 | (2006.01) |

(52) U.S. Cl.
CPC ............. *A61B 3/14* (2013.01); *A61F 9/008* (2013.01); *A61B 3/152* (2013.01);
(Continued)

(58) Field of Classification Search
CPC ........................................... A61F 9/008
See application file for complete search history.

(56) References Cited

U.S. PATENT DOCUMENTS

| 3,703,176 A | 11/1972 | Vassiliadis et al. |
| 4,884,884 A | 12/1989 | Reis |
(Continued)

FOREIGN PATENT DOCUMENTS

| JP | 2004-229965 A | 8/2004 |
| WO | 2000/021475 A1 | 4/2000 |

OTHER PUBLICATIONS

Barrett et al., "Computer-Aided Retinal Photocoagulation System", Jan. 1996, Journal of Biomedical Optics, vol. 1, No. 1, pp. 83-91.
(Continued)

*Primary Examiner* — Lynsey C Eiseman
(74) *Attorney, Agent, or Firm* — Kilpatrick Townsend & Stockton LLP

(57) ABSTRACT

A photomedical system and method for treating and/or diagnosing a patient's eye that includes a first light source for producing light, a scanning device for deflecting the light to produce a pattern of the light on the eye, a viewing element positioned to view the eye by a user or physician, and an alignment element aligned to the viewing element and the scanning device for optically indicating through the viewing element a location on the eye on which the pattern of the light will be located, but without projecting any alignment light onto the eye.

12 Claims, 12 Drawing Sheets

Related U.S. Application Data

(60) Provisional application No. 60/731,618, filed on Oct. 28, 2005.

(52) U.S. Cl.
CPC ........... *A61F 2009/00851* (2013.01); *A61F 2009/00863* (2013.01); *A61F 2009/00897* (2013.01)

(56) References Cited

U.S. PATENT DOCUMENTS

| | | | |
|---|---|---|---|
| 4,887,592 A | 12/1989 | Loertscher | |
| 4,917,486 A | 4/1990 | Raven et al. | |
| 5,057,102 A | 10/1991 | Tomioka et al. | |
| 5,098,426 A * | 3/1992 | Sklar | A61F 9/008 606/5 |
| 5,214,455 A | 5/1993 | Penney et al. | |
| 5,307,096 A | 4/1994 | Baroth et al. | |
| 5,337,095 A | 8/1994 | Katsuragi et al. | |
| 5,488,443 A | 1/1996 | Ota et al. | |
| 5,502,521 A | 3/1996 | Katou | |
| 5,532,769 A | 7/1996 | Miwa et al. | |
| 5,543,866 A | 8/1996 | Van de Velde | |
| 5,568,208 A | 10/1996 | Van de Velde | |
| 5,644,375 A | 7/1997 | Suzuki | |
| 5,743,902 A | 4/1998 | Trost | |
| 5,861,955 A | 1/1999 | Gordon | |
| 5,873,832 A | 2/1999 | Maloney et al. | |
| 5,892,569 A | 4/1999 | Van de Velde | |
| 5,921,981 A | 7/1999 | Bahmanyar et al. | |
| 5,943,117 A | 8/1999 | Van de Velde | |
| 5,957,915 A | 9/1999 | Trost | |
| 5,971,978 A | 10/1999 | Mukai | |
| 5,980,513 A | 11/1999 | Frey et al. | |
| 6,004,313 A | 12/1999 | Shimmick et al. | |
| 6,066,128 A | 5/2000 | Bahmanyar et al. | |
| 6,096,028 A | 8/2000 | Bahmanyar et al. | |
| 6,099,522 A | 8/2000 | Knopp et al. | |
| 6,149,643 A | 11/2000 | Herekar et al. | |
| 6,149,644 A | 11/2000 | Xie | |
| 6,165,142 A | 12/2000 | Bar | |
| 6,186,628 B1 | 2/2001 | Van de Velde | |
| 6,234,632 B1 | 5/2001 | Nakao | |
| 6,238,385 B1 | 5/2001 | Harino et al. | |
| 6,267,756 B1 | 7/2001 | Feuerstein et al. | |
| 6,328,733 B1 | 12/2001 | Trost | |
| 6,347,244 B1 | 2/2002 | Dubnack | |
| 6,394,999 B1 | 5/2002 | Williams et al. | |
| 6,494,878 B1 | 12/2002 | Pawlowski et al. | |
| 6,771,423 B2 | 8/2004 | Geist | |
| 6,789,900 B2 | 9/2004 | Van de Velde | |
| 7,146,983 B1 | 12/2006 | Hohla et al. | |
| 7,301,644 B2 | 11/2007 | Knighton et al. | |
| 2002/0036749 A1 | 3/2002 | Isogai | |
| 2002/0167462 A1 | 11/2002 | Lewis et al. | |
| 2003/0009155 A1 | 1/2003 | Pawlowski et al. | |
| 2004/0059321 A1 | 3/2004 | Knopp et al. | |
| 2004/0186462 A1 | 9/2004 | Murakami | |
| 2005/0046794 A1 | 3/2005 | Silvestrini et al. | |
| 2006/0100677 A1 | 5/2006 | Blumenkranz et al. | |
| 2006/0118263 A1 | 6/2006 | Silvestrini | |
| 2006/0184243 A1 | 8/2006 | Yilmaz | |
| 2006/0271026 A1 | 11/2006 | Silvestrini et al. | |
| 2008/0015553 A1 | 1/2008 | Zacharias | |
| 2008/0249512 A1 | 10/2008 | Van saarloos et al. | |

OTHER PUBLICATIONS

Barrett et al., "Digital Imaging-Based Retinal Photocoagulation System", Feb. 8, 1997, SPIE, vol. 2971, pp. 118-128.

Extended European Search Report received for European Patent Application No. 06827186.5, dated Jul. 22, 2009, 4 pages.

International Preliminary Report on Patentability received for PCT Patent Application No. PCT/US2006/042497, dated Apr. 29, 2008, 6 pages.

International Search Report and Written Opinion received for PCT Patent Application No. PCT/US2006/042497, dated Aug. 8, 2007, 6 pages.

Markow et al., "An Automated Laser System for Eye Surgery", IEEE Engineering in Medicine and Biology Magazine, Dec. 1989, pp. 24-29.

Naess et al., "Computer-assisted laser photocoagulation of the retina-a hybrid tracking approach", Journal of Biomedical Optics, vol. 7, No. 2, Apr. 2002, pp. 179-189.

Office Action received for Indian Patent Application No. 2663/CHENP/2008, dated Dec. 24, 2013, 2 pages.

Van De Velde, "Role of the Scanning Laser Ophthalmoscope in Photodynamic Therapy of Macular Disease", Ophthalmic Technologies X, Proceedings of SPIE, vol. 3908, 2000, pp. 190-201.

Wright et al., "Hybrid Approach to Retinal Tracking and Laser Aiming for Photocoagulation", Journal of Biomedical Optics, vol. 2, No. 2, Apr. 1997, pp. 195-203.

Wright et al., "Initial In Vivo Results of a Hybrid Retinal Photocoagulation System", Journal of Biomedical Optics, vol. 5, No. 1, Jan. 2000, pp. 56-61.

* cited by examiner

PHOTOMEDICAL TREATMENT SYSTEM AND METHOD WITH A VIRTUAL AIMING DEVICE

CROSS-REFERENCE TO RELATED APPLICATION(S)

This application is a continuation of U.S. Ser. No. 11/588,451, filed on Oct. 27, 2006, which claims the benefit of priority under 35 U.S.C. § 119(e) of U.S. Ser. No. 60/731,618, filed on Oct. 28, 2005. The content of both applications are hereby incorporated by reference in their entirety for all purposes.

BACKGROUND OF THE INVENTION

Field of the Invention

The present invention provides apparatus, method and system for photomedical treatment using an optical system.

Background Information

Ophthalmic laser treatment is widely used today to treat various conditions such as diabetic retinopathy and age-related macular degeneration. Typically, multiple spot laser therapy is performed by utilizing slit-lamp delivery or probes that are inserted into the eye. In a slit-lamp-mounted laser delivery device, the slit lamp is arranged to allow easy illumination and microscopic viewing of the eye of a seated patient. Slit lamps used in laser treatment/surgery include a high-brightness illuminator and microscope mounted on a shared pivot point. This arrangement allows the viewing angle of the microscope and illuminator to be changed as often as desired without moving the field of illumination or visualization.

Laser treatment/surgery requires high precision laser beam aiming, and often uses an aiming beam to create an alignment pattern to "mark" the target area on or within the patient's eye. Commonly, the separate aiming beam and the treatment beam are combined to propagate in a shared path, and both are projected onto the target tissue in the patient's eye. The physician, who is viewing the patient's eye, moves the alignment pattern onto the desired target tissue. The treatment beam which is coincident with the alignment pattern is then activated. In this configuration, the alignment pattern (which can be one or more spots, or a scanned image), is a "real" image because it is an actual pattern of light intentionally projected onto (and subsequently viewed from) the actual target tissue.

While the use of an aiming beam that is coincident with the treatment beam at the targeted eye structure works well in most situations, it has its shortcomings. For example, because the aiming beam is optically coupled to the patient's eye, the patient sees the alignment pattern before and/or during treatment. There may also be associated safety and/or patient discomfort issues because the aiming beam irradiance is in general higher in the patient's eye than in the physician's eye. In some procedures, it is preferable for the patient to not see the aiming beam. An ophthalmic laser treatment/surgery technique and device that allows the physician but not the patient to see the alignment pattern is desired.

SUMMARY OF THE INVENTION

The present invention solves the aforementioned problems by providing a photomedical system and technique for treating and/or diagnosing a patient's eye, which generates an alignment pattern for the physician or user, but without the necessity of projecting aiming beam light onto the eye.

A photomedical system for treating and/or diagnosing a patient's eye includes a first light source for producing light, a scanning device for deflecting the light to produce a pattern of the light on the eye, a viewing element positioned to view the eye, and an alignment element aligned to the viewing element and the scanning device for optically indicating through the viewing element a location on the eye on which the pattern of the light will be located without projecting alignment light onto the eye.

A photomedical system for treating and/or diagnosing a target object can also include a light source for producing light, a pattern generation unit for directing a pattern of the light to the target object, a viewing element positioned to view the target object, an alignment element optically coupled to the viewing element for defining a treatment zone on the target object, and a controller for controlling the pattern generation unit to direct the pattern of the light only within the treatment zone of the target object.

A method of performing a photomedical treatment or diagnosis of a target object includes generating an image of the target object on a viewing element, generating a virtual alignment pattern on the viewing element, without projecting the virtual alignment image onto the target object, to define a treatment zone of the target object, generating light, and projecting the light onto the target object and only within the treatment zone defined by the virtual alignment pattern.

Other objects and features of the present invention will become apparent by a review of the specification, claims and appended figures.

DETAILED DESCRIPTION OF THE INVENTION

Figure 1:
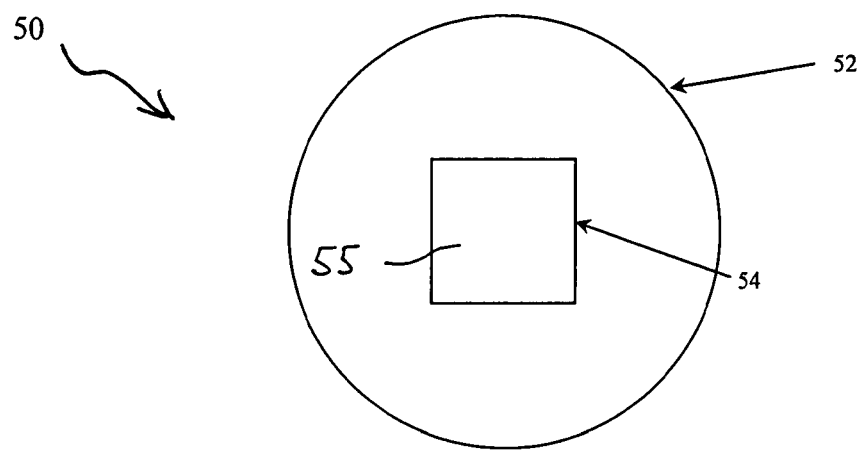
FIG. 1 illustrates a square shaped virtual alignment pattern that defines a treatment zone within a visualized area of tissue.

As described above, a typical photomedical treatment entails projecting an aiming beam directly onto the target tissue (e.g., a structure on or within a patient's eye) to generate an alignment pattern thereon. A pattern can be one or more stationary or moving spots, or an image or shaped object scanned or otherwise created. A physician can see the projected aiming beam alignment pattern on the patient's eye, and align this pattern to the desired target tissue thus aligning the treatment beam(s) which are coincident therewith. With this treatment method, the patient also sees the aiming beam alignment pattern. The treatment/diagnosis method of the invention employs an aiming device that is optically coupled primarily to the physician's eye and not the patient's eye. This is accomplished by generating a virtual alignment pattern that the physician can see and use to align the treatment beam(s), but without projecting the alignment pattern onto the target tissue. Thus, while the physician sees an image of the patient's eye shared with an alignment pattern superimposed thereon, the patient does not see the alignment pattern. The system of the invention achieves this sharing of the eye image with the alignment pattern by using a virtual alignment pattern located at an image plane that is conjugate to the targeted eye structure.

As used herein, a "real" alignment pattern is one in which aiming beam light is actually projected onto the target tissue, and which is subsequently scattered and/or reflected from the target tissue and viewed by the physician or user. A "virtual" alignment pattern is one which aiming beam light is superimposed onto the view of the target tissue but without projecting this light pattern onto the tissue itself. The virtual alignment pattern does not rely upon the interaction of the aiming beam light with the targeted tissue in order for the physician or user to obtain a view of the alignment pattern.

One way to create a virtual alignment pattern superimposed on an image of target tissue is to employ a physical pattern in an alignment element as part of the visual aiming device, where a physical pattern is placed in the optical train between the tissue and either the physician's eye or the image capturing device. FIGS. 1 through 6B illustrate examples of virtual alignment patterns 54 that may be used with the system of the invention to outline or otherwise identify treatment zones 55 within visualized areas 52 of the target tissue. FIGS. 8-12 and 16 are schematic diagrams of systems using physical patterns to create a virtual alignment pattern. FIG. 7 illustrates the virtual alignment pattern 54 superimposed on the visualized area 52 of tissue thus defining the treatment zone 55 in which the treatment beams 56 are applied.

FIG. 1 shows a first embodiment of the virtual alignment pattern. In the physician's view 50 of the visualized area 52 of the target tissue, a virtual alignment pattern 54 is superimposed thereon to define a treatment zone 55 within the visualized area 52 of the tissue. The visualized area 52 is a general region of the patient's retina including the part that needs to be treated, and the treatment zone 55 is where the treatment beam(s) are to be aimed. As will be described later, a user of the system positions the virtual alignment pattern 54 over the desired part of the target object for treatment before the treatment beam(s) are activated. In the embodiment of FIG. 1, the treatment zone 55 has a rectangular shape. The physical pattern used to generate the virtual alignment pattern 54 is positioned within the system such that all the treatment beam(s) are projected only onto target tissue within the treatment zone 55 defined by the virtual alignment pattern 54.

Figure 2:
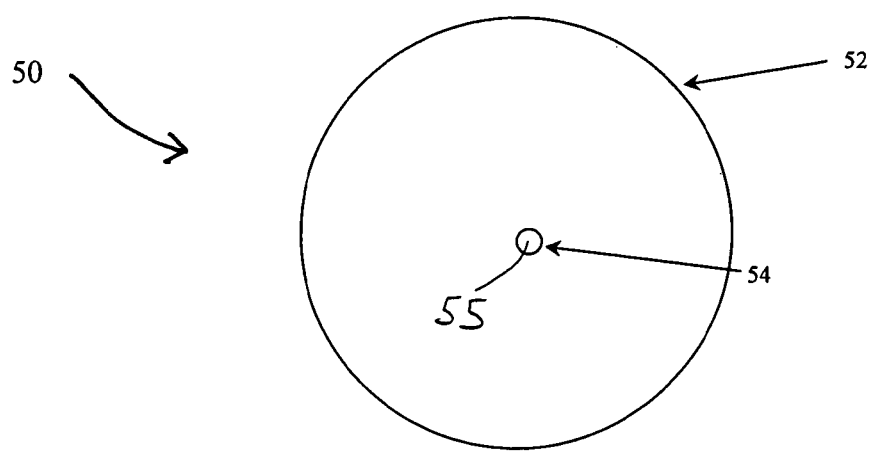
FIG. 2 illustrates a circular shaped virtual alignment pattern that defines a treatment zone within a visualized area of tissue.
Figure 3:
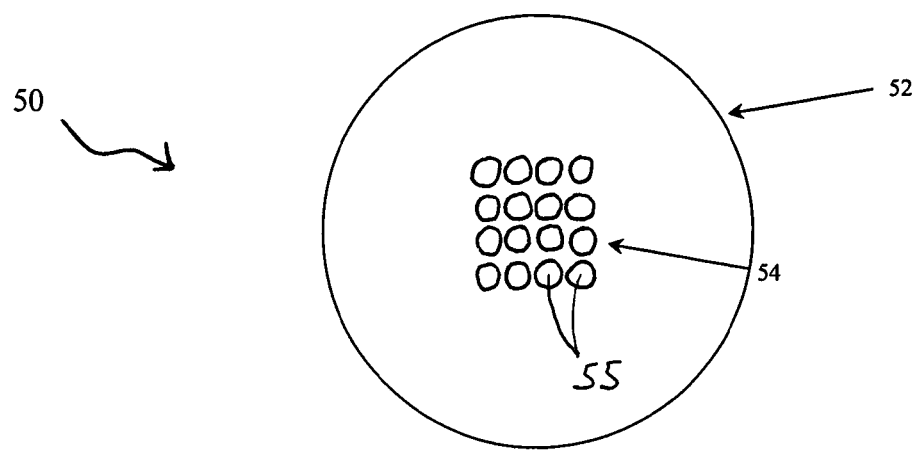
FIG. 3 illustrates a virtual alignment pattern of a plurality of spots that defines treatment zones within a visualized area of tissue.
Figure 4:
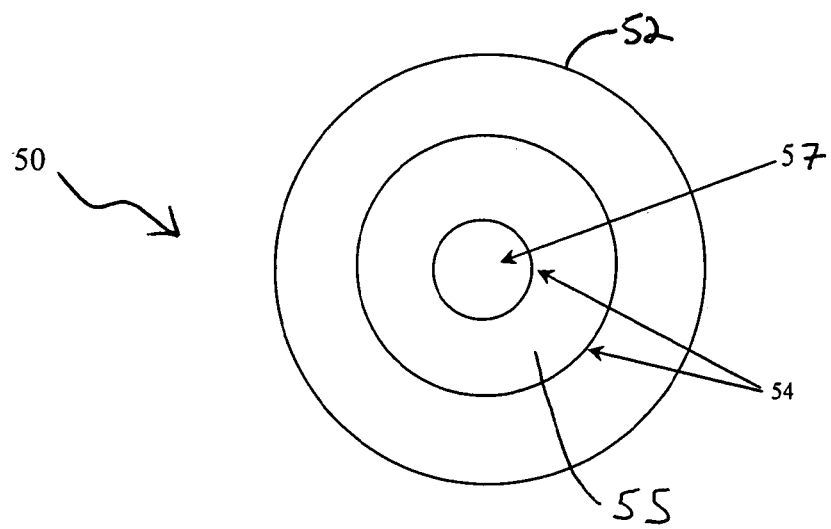
FIG. 4 illustrates an annular shaped virtual alignment pattern that defines a treatment zone Within a visualized area of tissue.

FIG. 2 shows a second embodiment of the virtual alignment pattern 54, wherein the treatment zone 55 defined thereby is a single circular spot. FIG. 3 shows a third embodiment of the virtual alignment pattern 54, wherein the treatment zones 54 defined there by is an array of spots. FIG. 4 shows a fourth embodiment of the virtual alignment pattern 54, wherein the treatment zone 54 defined thereby has an annular shape such that a central portion 57 is untreated. This annular shaped treatment zone 55 may be used, for example, in photocoagulation about the fovea.

Figure 5:
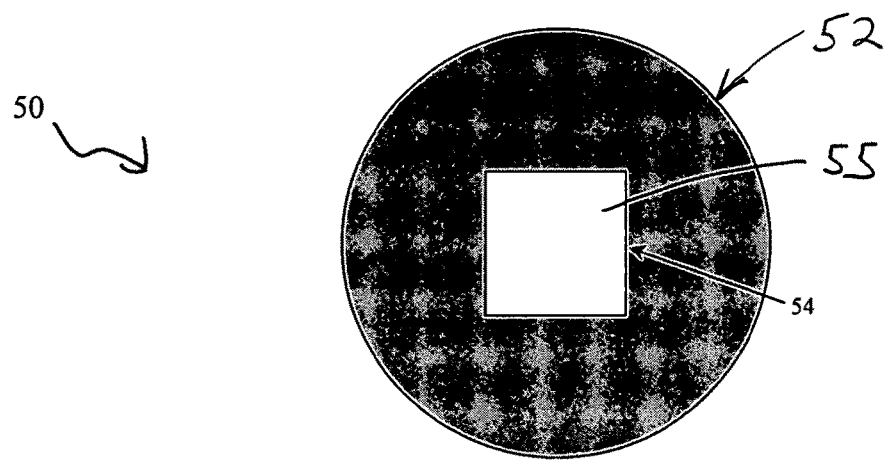
FIG. 5 illustrates a square shaped virtual alignment pattern with shading that defines a treatment zone within a visualized area of tissue.

FIG. 5 shows a fifth embodiment of the virtual alignment pattern 54, wherein a shading or a different color is used outside of the treatment zone 55 to more clearly distinguish the outer boundaries thereof. The shape and size of the treatment zone 55 in FIG. 5 is substantially the same-as that in FIG. 1. However, the shading/coloring provides enhanced visual contrast between the treatment zone 55 and the rest of the visualized area 52.

Figures 6A, 6B:
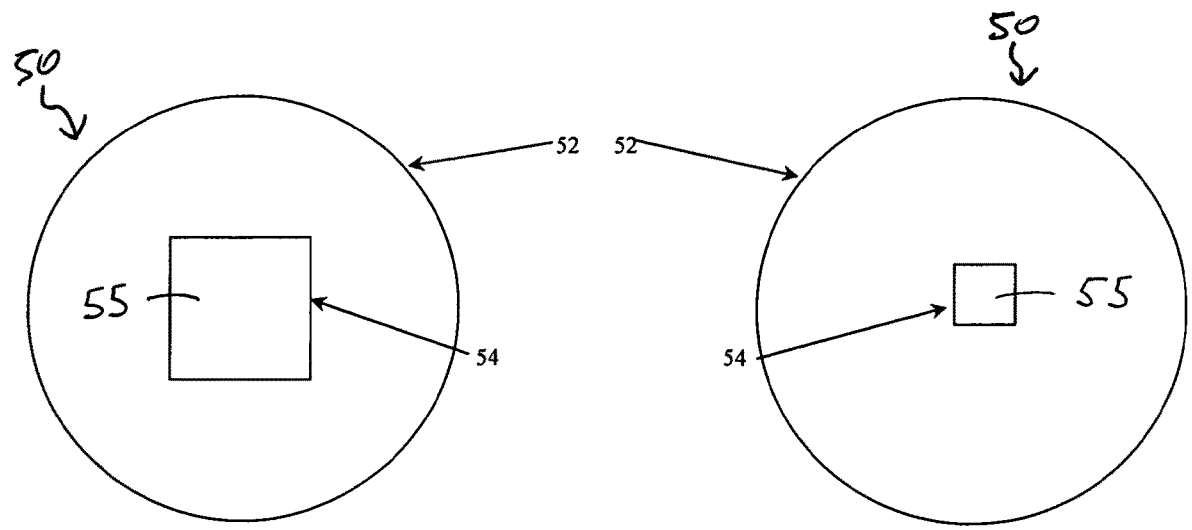
FIGS. 6A and 6B illustrate varying sizes of a square shaped virtual alignment pattern that defines a treatment zone within a visualized area of tissue.
Figure 7:
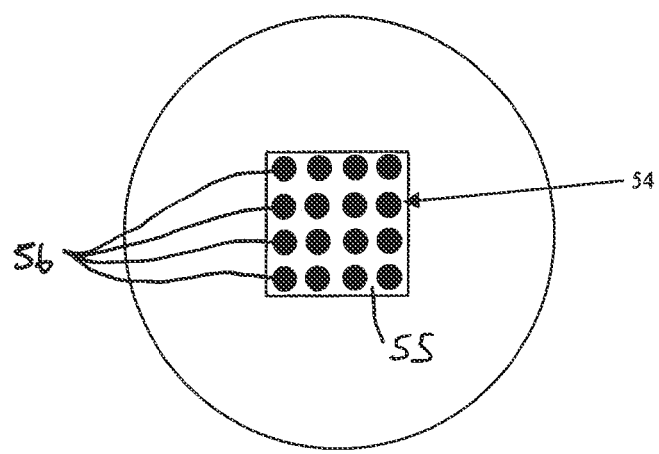
FIG. 7 illustrates treatments spots within the treatment zone outlined by a square virtual alignment pattern.

FIGS. 6A and 6B illustrate how the size of the alignment pattern 54 and thus the treatment zone 55 defined thereby is changeable within the same visualized area 52. This change in size can be affected by reducing the size the alignment pattern 54, which will automatically coincide with a reduction in the size of the treatment zone 55 treated by the treatment beam(s).

FIG. 7 shows an image of the patient's eye as viewed by the user (physician) during treatment shared with the virtual alignment pattern of FIG. 1. The shared image shows the treatment spots 56 in the treatment zone 55. The laser source, or its scanner, is calibrated to only treat that portion of the tissue falling within the boundaries of the treatment zone 55 as defined by the virtual alignment pattern 54. In the particular example of FIG. 7, the treatment beams 56 are programmed to evenly fill the treatment zone 55. A scanned beam may be positioned onto the corners of the treatment zone 55, and data may be stored to define the maximum allowed treatment pattern boundaries. With the imaging system fixed both in position and magnification, the location of the treatment beam spots within the visualized area 52 can be accurately controlled. The treatment beam(s) may then be automatically delivered to stay within the confines of the visible boundaries of the treatment zone 55. With the use of the virtual alignment pattern 54, an aiming beam projected onto the target tissue is unnecessary to accurately direct the treatment beam(s) to the proper locations on the target tissue.

Figure 8:
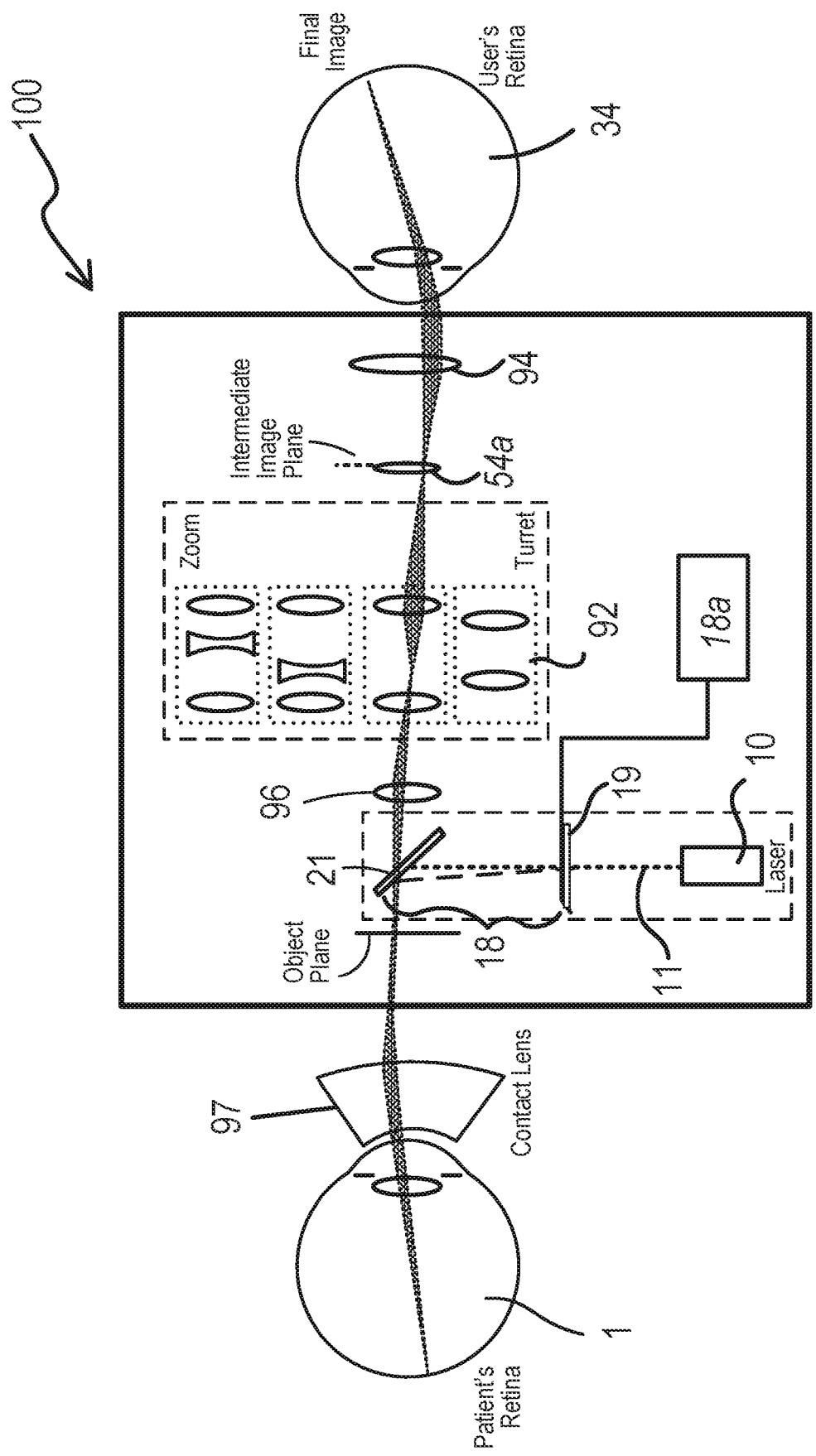
FIG. 8 is a schematic diagram of a first embodiment of the photomedical treatment system.

FIG. 8 is a schematic diagram of a first embodiment of the photomedical treatment system 100, which employs a virtual alignment pattern. As shown, the photomedical treatment system 100 includes a treatment/diagnostic light source 10, a variable magnification unit 92 (e.g., as within a microscope), and the alignment element 54a with a physical pattern used to generate the virtual alignment pattern 54. An objective lens 96, which may be infinity-corrected, is located between the magnification unit 92 and a pattern generation unit 18. The alignment element 54*a* can be any moving or stationary blockage, tinting, shaped aperture, scribed or imprinted optic or window, LCD screen, etc. through which the image of the target tissue is viewed. A simple example is scribing or imprinting spots or lines on an optical element such as a lens or transparent window. The alignment element may be illuminated so that it is visible to the user only by the light associated with the microscope illumination returning from the patient's eye, or by a dedicated alignment element light source, or by light self-generated by the alignment element. A user's eye 34 (e.g., a physician's eye) views a target object 1 through a viewing element 94 and the alignment element 54*a*. The pattern generation unit 18 is aligned with the alignment element 54*a* such that it projects the treatment beam(s) only onto that portion of the target object 1 that is viewable through the alignment element 54*a* (and thus is contained within the virtual alignment pattern 54). Preferably, the alignment element 54*a* is positioned at the intermediate image plane of the variable magnification unit 92. The pattern generation unit 18 can include one or more moving optical elements (using galvos, piezo electric devices, motors, etc.) as part of a scanner 19 that scans spots, lines or shapes of treatment light onto the object 1. In its simplest form, pattern generation unit 18 can image a single, non-moving spot onto the object 1. In a more complicated form, pattern generation unit 18 can adjust the size/extent of the treatment pattern to coincide with the target region displayed to the user at the selected magnification.

In operation, the user aligns the target object 1 to the system 100 (or vice versa) so that the tissue intended to be treated is positioned inside the area viewable inside the virtual alignment pattern 54 (as dictated by alignment element 54*a*). Specifically, the area of tissue for treatment is positioned inside the virtual alignment pattern 54 as viewed through viewing element 94. The user also sets up the controller unit 18*a* for the pattern generation unit 18 so that the treatment beam is of a desired shape, size, and/or pattern within the virtual alignment pattern 54. Then, while viewing the visualized area 52 of the target object 1, the user activates the light source 10 to produce a treatment beam 11. If the treatment requires multiple spots or a scanned image/shape, the treatment beam 11 is converted to multiple beams or beams of the desired shape by a pattern generation unit 18. The pattern generation unit 18 may convert the treatment beam 11 to one or more treatment beams by either temporal or spatial division. In the particular embodiment of FIG. 8, the pattern generation unit 18 includes scanner 19 and a mirror 21. The scanner 19 creates sequential or multiple treatment beams, and the mirror 21 directs the treatment beams to the part of the target object 1 that is within the intended treatment zone 55 as defined by the virtual alignment pattern 54. The user's view of the visualized area 52 is enhanced by a viewing element 94 (e.g. a lens), magnification unit 92, lens 96, and a contact lens 97 that may be used in contact with the object 1. The treatment/diagnostic light source 10 may be a diode-pumped solid state laser, gaseous laser, semiconductor laser, light emitting diode, flash lamp, etc.

In this embodiment, the virtual alignment pattern 54 is imaged directly into the user's eye (via the alignment element 54*a*) without projecting the alignment pattern onto the object 1. Thus, the treatment beam(s) are easily and accurately aligned to the target tissue simply by aligning that tissue to the virtual alignment pattern 54, where the treatment beam(s) will be seen as overlaid on the treatment zone 55, defined by the alignment pattern 54.

The variable magnification unit 92 is a well known device that includes multiple sets of optics that can be interchanged to achieve the desired magnification level. For example, the interchangeable optics may be mounted in a turret-style configuration where the sets of optics are rotated and locked into position as in a laboratory-style microscope. The magnification selection can be utilized by the controller 18*a* if necessary to ensure that the treatment zone 55 as defined by the virtual alignment pattern 54 and viewed by the user is fully filled with the treatment beam(s).

Figure 9:
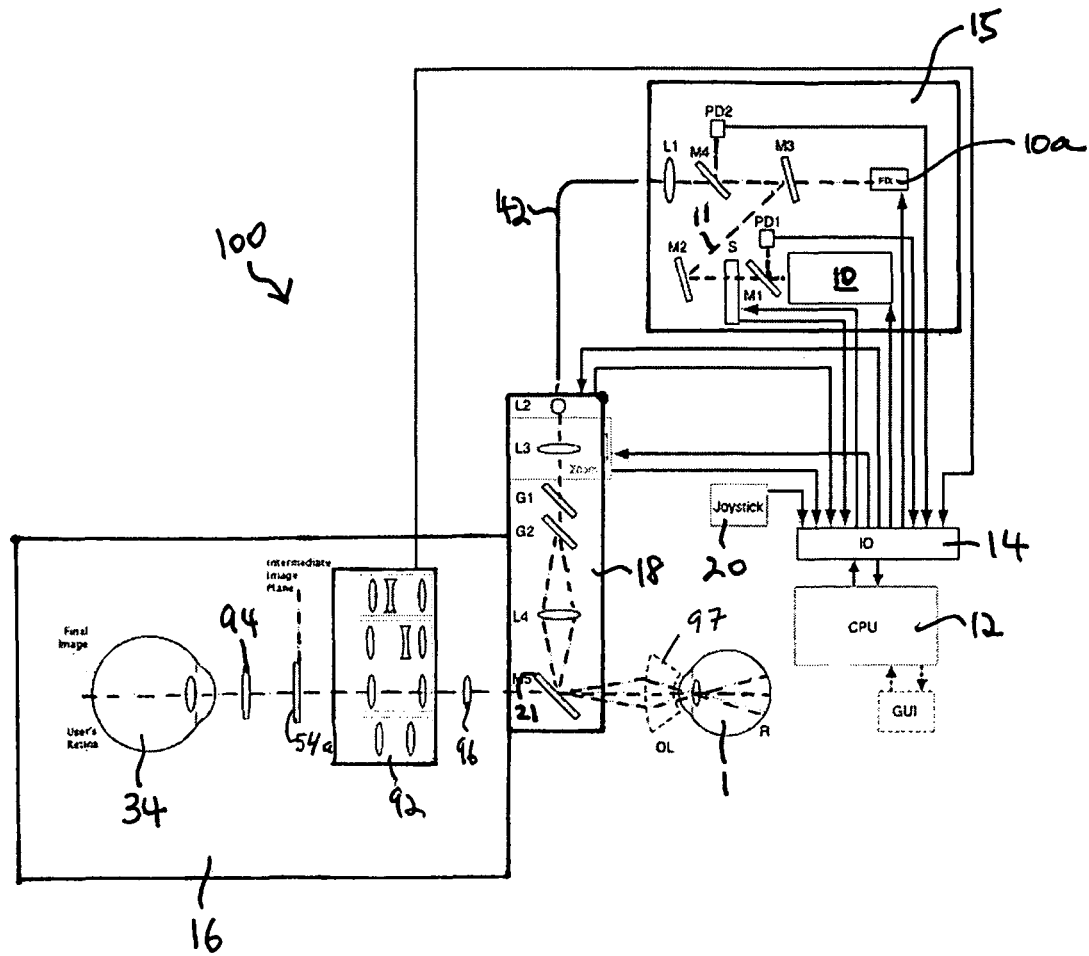
FIG. 9 is a schematic diagram of a second embodiment of the photomedical treatment system.

FIG. 9 is a schematic diagram of a photomedical system 100 in accordance with a second embodiment of the invention, which is similar to that of FIG. 8, but additionally includes a fiber unit 42 for optical beam delivery, a fixation source 10*a* to help minimize the patient's eye movement, and a more complex pattern generation unit 18. The photomedical system 100 includes a CPU 12, an input/output device 14, a light generation unit 15, an imaging unit 16, and the pattern generation unit 18. The CPU 12 controls the light generation unit 15, the imaging unit 16, and the pattern generation unit 18 via the input/output device 14. The user 34 views the treatment site of the target object 1 via the imaging unit 16. The CPU 12 may be a microprocessor, microcontroller, or any other type of suitable control electronics. A slit lamp microscope illumination device may be added for better illumination of (and viewing of) the target eye tissue.

As shown, the light generation unit 15 is optically coupled to the pattern generation unit 18 by a fiber unit 42, thus allowing these units to be physically separated. The combining mirror 21 of the pattern generation unit 18 directs the treatment beam(s) 11 to the target object 1. The user 34, who views the visualized area 52 of the target object 1 through the objective lens 96, the variable magnification device 92, and the alignment element 54*a* of the imaging unit 16, sees a shared image of the treatment beam spots in the treatment zone 54. The alignment element 54*a* is preferably placed at the intermediate image plane of the variable magnification device 92.

The light generation unit 15 includes the target/diagnostic light source 10. The light source 10 is controlled by the CPU 12 via the input and output (I/O) device 14 to generate the treatment beam 11, whose centerline is shown by dashed lines. The treatment beam 11, upon being generated by the light source 10, encounters mirror M1 which directs a first portion of the treatment beam 11 to a photodiode PD1. The photodiode PD1 may be replaced with other types of sensors, as appropriate. The photodiode PD1 serves to sample and measure the power of the light for safety purposes. A second portion of the light from the mirror M1 that is not directed to the photodiode PD1 goes to a shutter S, which acts as a gate to the treatment beam 11. The shutter S controls the treatment beam 11 to produce discrete spots or a continuous supply of the optical beam to create continuous scans as a means to produce the desired treatment pattern. If the shutter S blocks the light, the treatment beam 11 does not travel any further. On the other hand, if the shutter S lets the light pass, the treatment beam 11 goes on to mirror M2 and mirror M3. Mirror M2 is a turning mirror that may be used in conjunction with mirror M3 and mirror M4 to align the treatment beam 11 into the fiber unit 42. A focusing lens L1 may be employed to help focus the treatment beam 11 into the fiber unit 42.

An optional a fixation beam light source 10*a* may be incorporated into the light generation unit 15 to provide an optical beam that helps "fixate" the patient's gaze during the treatment. The fixation beam generated by the fixation light beam source 10a utilizes the same optical path as the treatment beam 11 by passing through mirror M3 and being delivered through the fiber unit 42. A second photodiode PD2 may be used to sample the optical beam after the fixation beam is combined with the treatment beam path.

The pattern generation unit 18 receives the treatment beam 11 that traveled through the fiber unit 42. Lenses L2, L3, and L4 and a mirror 21 of the pattern generation array 18 function to direct the treatment beam 11 to the target object 1. Light exiting the optical fiber unit 42 first encounters lens L2 and becomes collimated before entering the lens L3. Lens L3 may be a single lens or a compound lens, and can be configured as a zoom lens for adjusting the intrinsic size of the beam that comprises the pattern. The lens L3 allows easy adjustment of the size of the pattern on the retina R, and is controlled by the CPU 12. The light coming out of the lens L3 passes through a pair of moving mirrors G1, G2 that either divide the treatment beam 11 into multiple beams or scan the treatment beam 11 in a treatment pattern. The treatment beams or pattern enter the lens L4, which images the optical midpoint of the scanner mirrors G1, G2 onto the mirror 21 to minimize the size of the mirror 21 in an attempt to increase the overall solid angle subtended by the pattern generation unit 18.

In operation, the user aligns the target object to the system 100 (or vice versa) and treats the object 1 as described above. The user may align the target tissue to the virtual alignment pattern using a user control unit 20, such as a joystick or a keyboard, and or with a graphic user interface (GUI).

Figure 10:
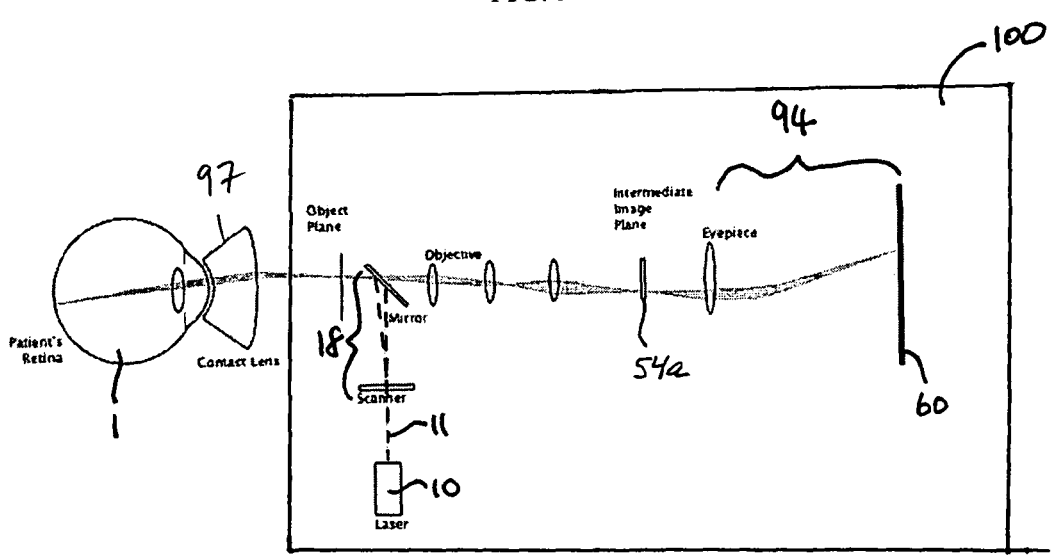
FIG. 10 is a schematic diagram of a third embodiment of the photomedical treatment system.

FIG. 10 is a schematic diagram of a third embodiment of the photomedical treatment system 100. In this embodiment, the viewing element 94 includes a camera or some other image-capturing device 60, such as a scanning laser ophthalmoscope or an optical coherence tomograph in addition to an eyepiece. As shown, an image collection device 60, instead of the user 34, "views" the target object 1 through the eyepiece. The collected image is then sent to a screen or a graphic user interface (GUI) for the user to view. The user 34, who indirectly views the target object 1 on the screen or the GUI, adjusts the position of the target tissue relative to the treatment zone 55 of the system (defined by the virtual alignment pattern 54), such that only that portion of target shown within the confines of the virtual alignment pattern 54 as viewed by the viewing element 94 will receive the treatment beam.

Figure 11:
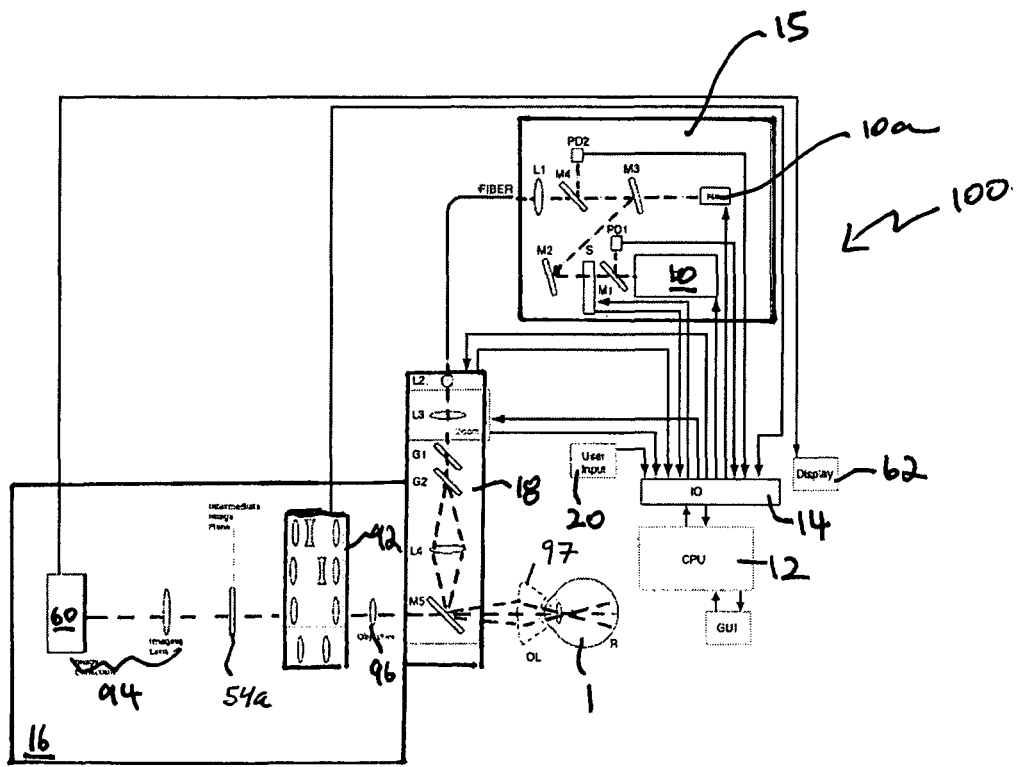
FIG. 11 is a schematic diagram of a fourth embodiment of the photomedical treatment system.
Figure 12:
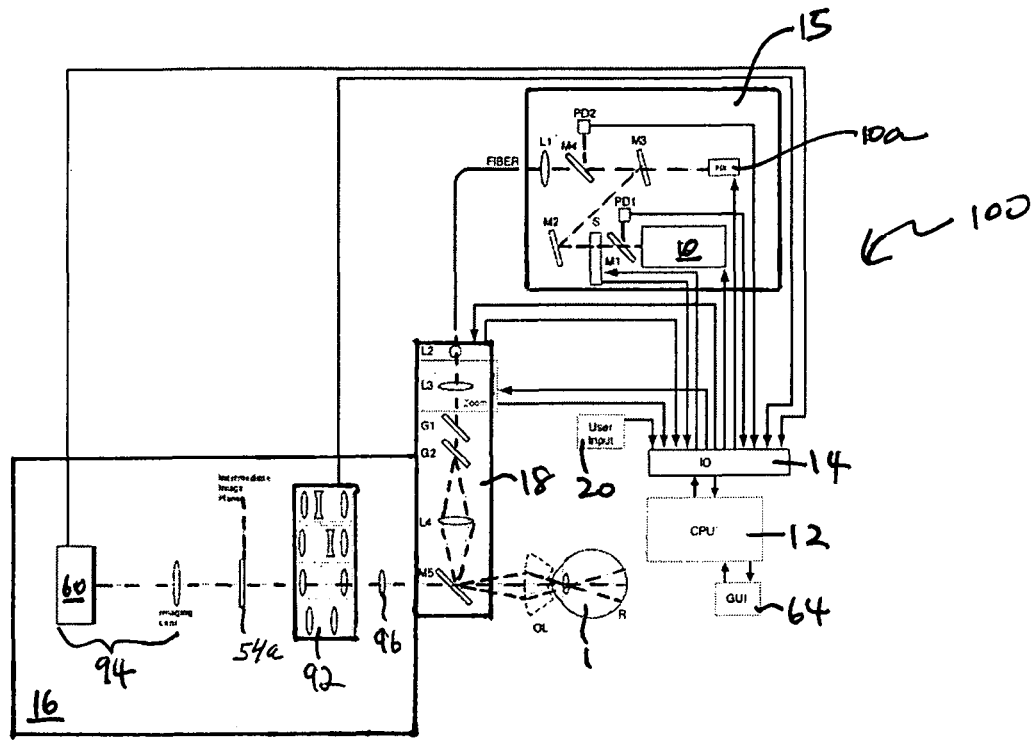
FIG. 12 is a schematic diagram of a fifth embodiment of the photomedical treatment system.

FIG. 11 is a schematic diagram of a fourth embodiment of the photomedical treatment system 100. This embodiment is a combination of the photomedical treatment system 100 of FIG. 9 and the imaging configuration of FIG. 10. As shown, the image collection device 60 is part of the viewing element 94 in this embodiment. The image "viewed" by the image collection device 60 is indirectly viewed by the user 34 through a display 62 (e.g., a monitor). FIG. 12 is a schematic diagram of a fifth embodiment of the photomedical treatment system 100. This embodiment is substantially similar to the fourth embodiment, except that it employs a GUI 64 and not a display 62 to display the image of the target object 1.

As described above, the mechanism for generating the virtual alignment pattern 54 is the use of a physical pattern disposed somewhere along the optical train between the targeted eye structure and the viewer. Such virtual alignment patterns are passive with respect to the light from the targeted tissue, in that the image from the target actually passes through the element that creates the pattern. However, the virtual alignment pattern can also be generated outside of this optical train, and projected onto the viewing element and therefore to the user (but not onto the target tissue) to define what portion of the object will receive the treatment beam(s), as follows.

Figure 13:
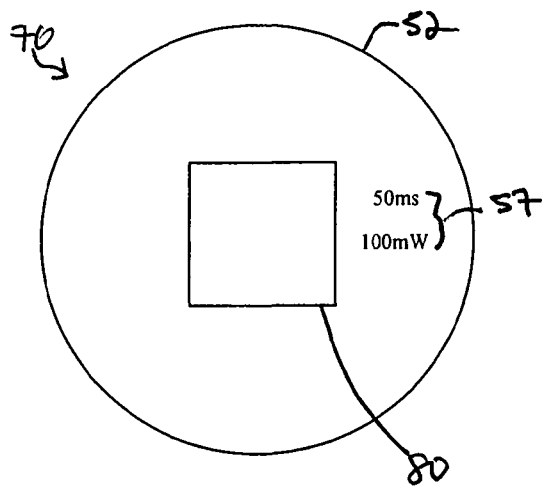
FIGS. 13 and 14 are examples of alignment elements that may be used with the system of the invention.
Figure 14:
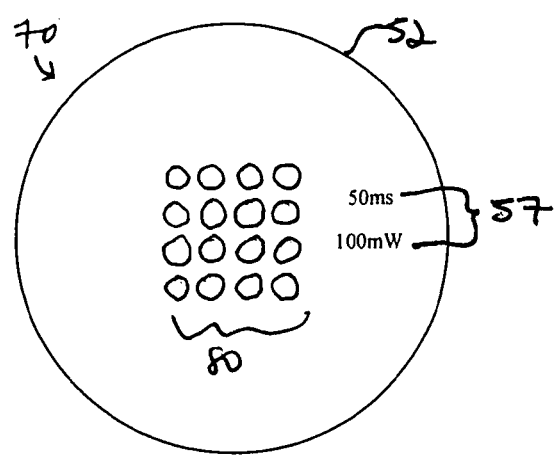

FIGS. 13 and 14 are exemplary physician's views 70 of the visualized area 52 of the target tissue, with a projected virtual alignment pattern 80 superimposed thereon. Projected virtual alignment patterns 80 have the same appearance and functionality of the patterns 54 described above, but differ in how they are generated. Instead of using a alignment element 54a in the optical train between the target tissue and viewer, a pattern of light is injected into the optical train and toward the user, so that only the user and not the patient can see light that forms the virtual alignment pattern 80. This approach of projecting the virtual alignment pattern could readily adapt to different microscope magnifications and/or spot/pattern sizes and shapes while still providing the same inherent accuracy as the static approach. This heads-up display configuration could also display system information 57 in the same view, such as the laser power, pulse duration, etc. by projecting the information onto the viewing element 94. Displaying the system information 57 provides convenience for the user, especially if the controls for the displayed parameters were made to be accessible without the need to look away from the patient.

Figure 15:
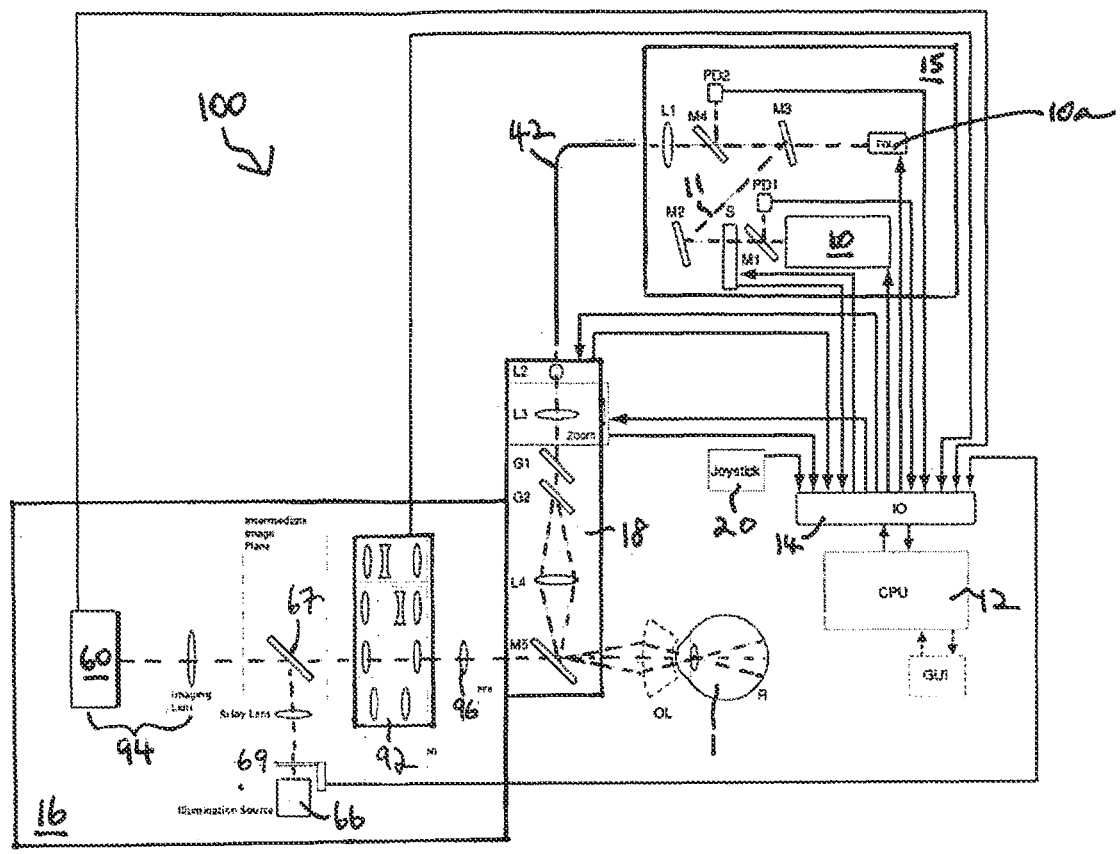
FIG. 15 is a schematic diagram of a sixth embodiment of the photomedical treatment system.

FIG. 15 is a schematic diagram of a sixth embodiment of the photomedical treatment system 100, utilizing a projected virtual alignment pattern 80. The general layout of the sixth embodiment is similar to the embodiment of FIG. 12, except that the alignment element 54a is replaced with a combining mirror 67, an alignment element 69, and an illumination source 66. An optional lens may also be used. The illumination source 66 provides a light beam that passes through the alignment element 69. The combining mirror 67 receives the pattern from the alignment element 69 and projects it onto the viewing element 94. Alignment element 69 can have the same possible configurations as alignment element 54a described above. Alternately, alignment element 69 can be incorporated as part of the illumination source 66, or could even be a moving element such as a scanner that generates patterns.

The viewing element 94 "sees" the projected virtual alignment pattern 80 on the target object 1 at the magnification level that is set by the variable magnification device 92. In this particular embodiment, the image collection device 60 forwards the "viewed" image to a screen for the user. The user is able to adjust the virtual alignment pattern 80 through the CPU 12, either to adjust the pattern itself and/or the location of the pattern on the image of the target object 1. Then, CPU 12 can adjusts the pattern generation unit 18 as necessary so that the treatment beam(s) are arranged to align with the projected virtual alignment pattern, and thereafter the light generation unit 15 is activated.

If the illumination source 66 generates broadband light, a broadband beamsplitter could be used as the combining mirror 67. However, doing so will reduce the amount of imaging light. Changing the illumination source to a single-color device would allow for the combining mirror to be a photopically balanced dichroic optical element that is matched to the illumination source to ameliorate the losses associated with using a broadband combiner.

Figure 16:
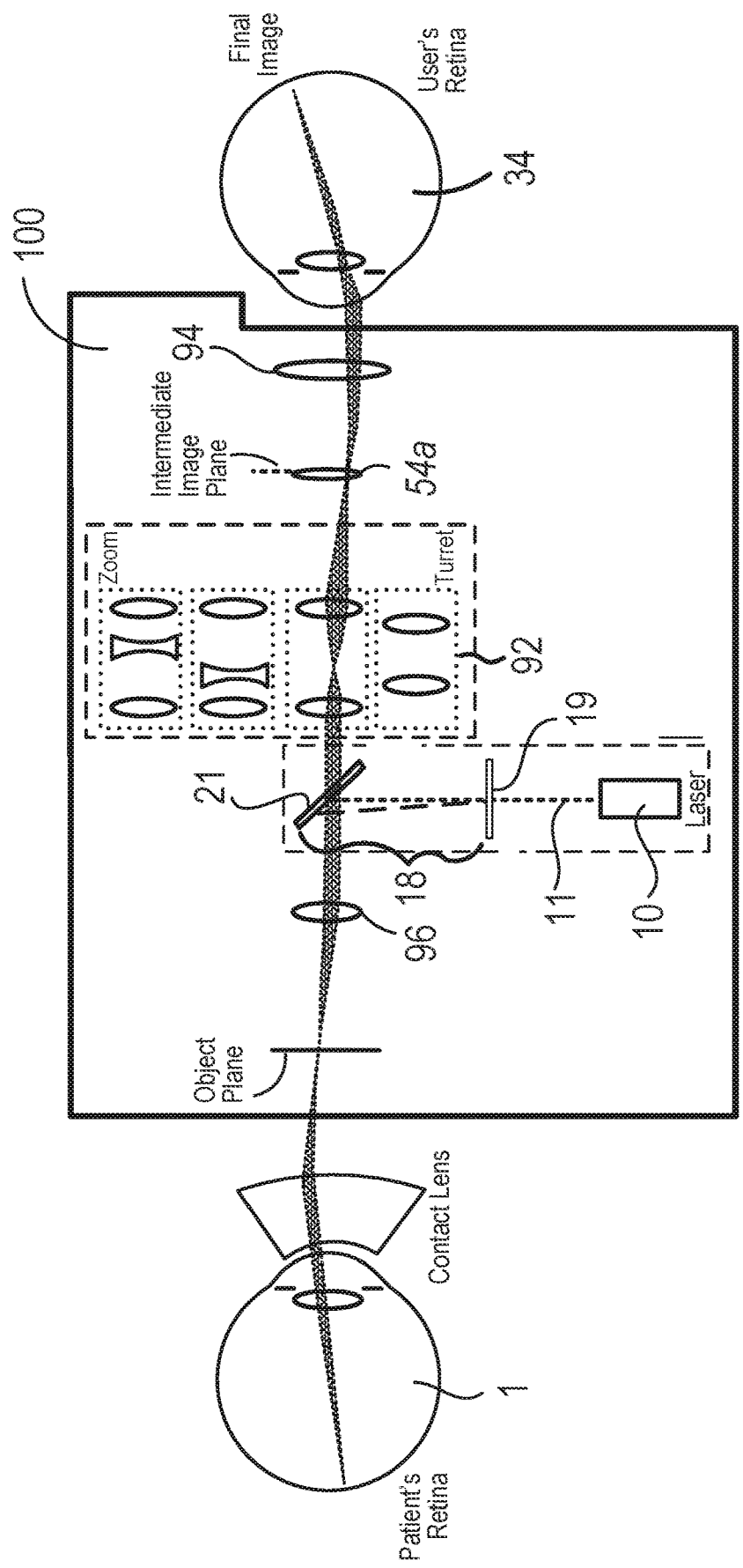
FIG. 16 is a schematic diagram of a seventh embodiment of the photomedical treatment system.
Figure 17:
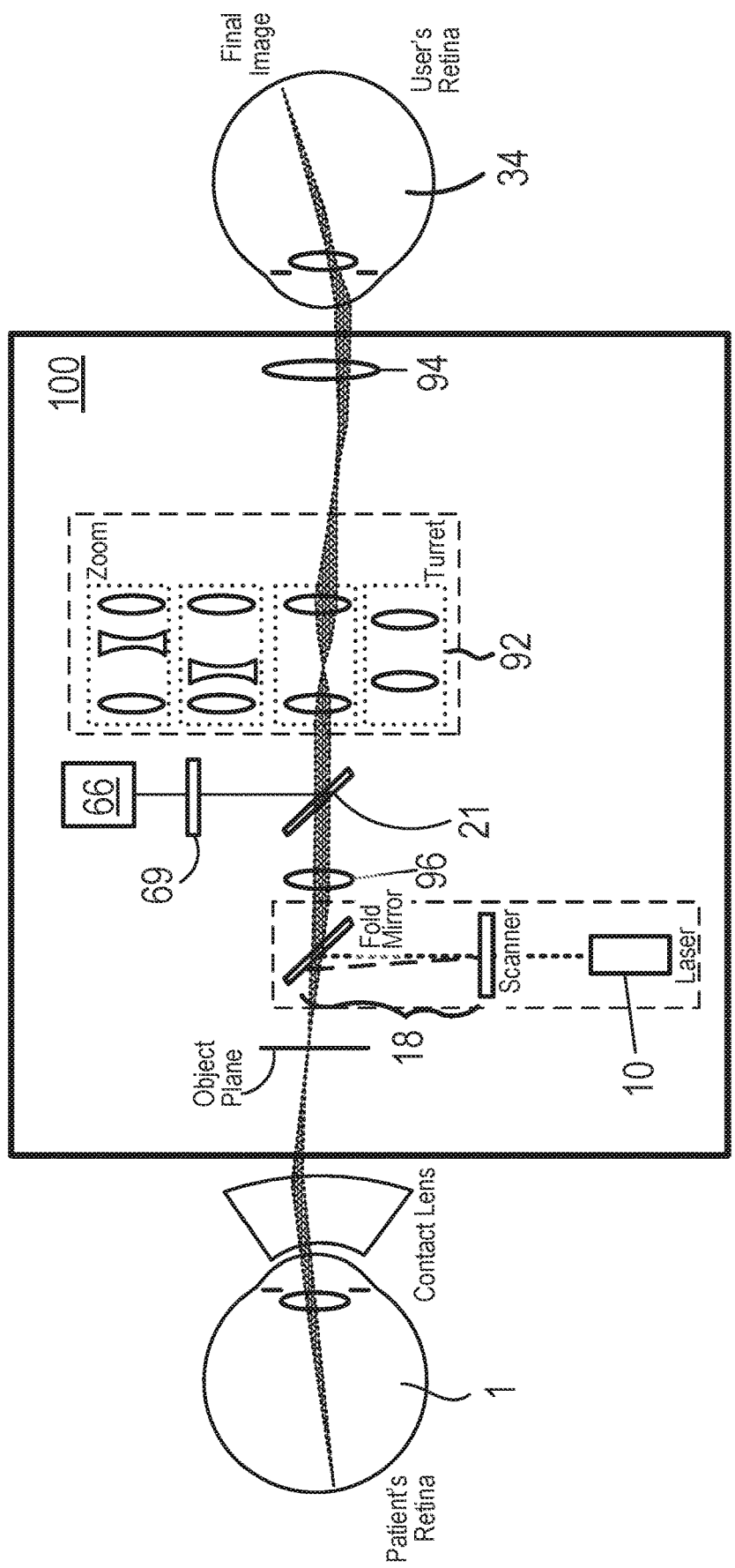
FIG. 17 is a schematic diagram of an eighth embodiment of the photomedical treatment system.
Figure 18:
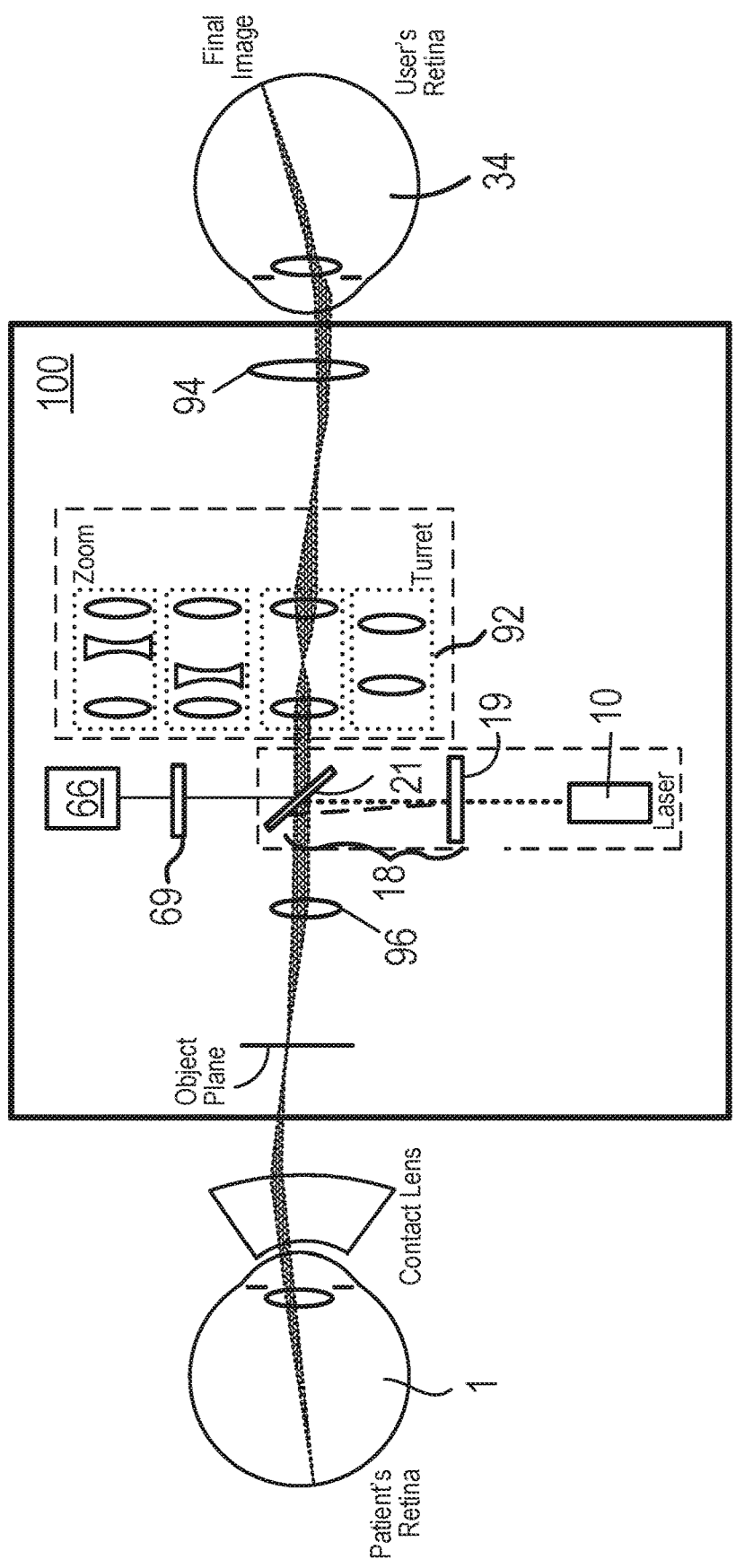
FIG. 18 is a schematic diagram of a ninth embodiment of the photomedical treatment system.

Although the invention has been described with reference to the above examples, it will be understood that modifications and variations are encompassed within the spirit and scope of the invention. For example, although the system is described as a photomedical treatment system, it may be used for diagnosis as well as treatment. Further, the specific order and/or combination of certain optical elements can change yet still achieve the goals of virtual alignment pattern and treatment beam overlap. For example, lens 96 in FIG. 9 can be moved to the patient's side of combining mirror 21, as illustrated in FIG. 16. The illumination sources 10 and 66 can be included in a single unit without optical fiber coupling, as illustrated in FIG. 17. The illumination sources 10 and 66 can be placed on opposite sides of a single combining mirror 21, as illustrated in FIG. 18. The physical pattern creating the virtual alignment pattern can be located anywhere that appropriately identifies the tissue aligned with the treatment beam(s), including integral to viewing element 94. Additionally, it should be understood that the description of the invention has concentrated upon the primary functions of the associated optical system. Secondary effects such as caused by ghosting reflections, scatter, back-scatter, or other causes of inadvertent or secondary projections or images are understood to be also present. Lastly, reference to treatment beams herein includes beams of wavelength and power effective for diagnosis as well. Accordingly, the invention is limited only by the following claims.

What is claimed is:

1. A photomedical system for treating an eye, the system comprising:
   an alignment element configured to generate a virtual alignment pattern;
   a treatment light source configured to generate treatment light;
   a pattern generator comprising a scanner optically coupled to the treatment light source, wherein the scanner is configured to deflect the treatment light onto target tissue of the eye as defined by the virtual alignment pattern;
   a viewing element comprising a lens, and configured to provide to the user both the virtual alignment pattern from the alignment element and system information superimposed on tissue of the eye, wherein overlapping areas of the displayed tissue of the eye and the virtual alignment pattern correspond to tissue of the eye to be targeted by the treatment light source;
   a controller communicatively coupled to the pattern generator and the viewing element, wherein the controller is configured to adjust parameters associated with at least one of a size, a shape, and an arrangement of the treatment light in order to position the treatment light to coincide with the virtual alignment pattern.

2. The photomedical system of claim 1, wherein the viewing element includes an electronic display.

3. The photomedical system of claim 1, wherein the viewing element includes an image-capturing device.

4. The photomedical system of claim 1, wherein the scanner is configured to divide the treatment light into a plurality of treatment beams.

5. The photomedical system of claim 4, wherein the scanner is configured to temporally sequence the plurality of treatment beams.

6. The photomedical system of claim 4, wherein the scanner is configured to spatially divide the plurality of treatment beams.

7. The photomedical system of claim 1, further comprising:
   a magnification device configured to adjustably magnify the displayed tissue of the eye as displayed by the viewing element.

8. The photomedical system of claim 1, further comprising:
   an illumination light source configured to generate illumination light of a single color.

9. The photomedical system of claim 8, wherein the viewing element includes a photopically balanced dichroic optical element having a transmission property that is matched to the single color of the illumination light.

10. The photomedical system of claim 1, wherein the pattern generator further comprises a combining mirror.

11. The photomedical system of claim 1, wherein the system information comprises a power of the treatment light.

12. The photomedical system of claim 1, wherein the system information comprises a pulse duration of the treatment light.

* * * * *